United States Patent
Stevens

(10) Patent No.: US 6,564,083 B2
(45) Date of Patent: May 13, 2003

(54) BONE MARROW EDEMA AS PREDICTIVE OF SUSCEPTIBILITY TO DEVELOPING PROGRESSIVE OSTEOARTHRITIS

(75) Inventor: Randall Marion Stevens, Union County, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/021,139

(22) Filed: Dec. 12, 2001

(65) Prior Publication Data

US 2002/0128548 A1 Sep. 12, 2002

Related U.S. Application Data

(60) Provisional application No. 60/256,264, filed on Dec. 18, 2000.

(51) Int. Cl.[7] .............................. A61B 5/055; A61B 5/00
(52) U.S. Cl. ........................................ 600/410; 128/898
(58) Field of Search ................................ 600/407, 410, 600/425; 128/898

(56) References Cited

PUBLICATIONS

Bollet, Alfred Jay, "Edema of the Bone Marrow Can Cause Pain in Osteoarthritis and Other Diseases of Bone and Joints", Apr. 3, 2001, Annals of Internal Medicine, vol. 134, No. 7, pp 591–593.*

Graif M., Schweitzer Me., *Skeletal Radiology*, 28(11), pp. 616–620 (1999).

Housten N., Schneller A., Lemke A., Schroder R., Felix R., *Orthopade*, 28(10), pp. 833–839 (1999).

Lieberman JM., Gardner CL., Motta AO., Schwartz RD., *Journal of Oral & Maxilifacial Surgery*, 54(4), pp. 434–439 (1996).

Stabler A., Glaser C., Reiser M., Resnick D., *European Radiology*, 9(8), pp. 1643–1646 (1999).

Tschauner C., Hofmann S., Urban M., Jaros S., Eder T., Czerny C., *Orthopade*, 27(11), pp. 765–771 (1998).

Yamamoto T., Bullough PG., *Arthritis & Reumatism* 43(11), pp. 2423–2427 (2000).

Yu JS., Dardani M., Fischer RA., *Journal of Computer Assisted Tomography*, 24(1), pp. 159–164 (2000).

Zanetti M., Bruder E., Romero J., Hodler J., *Radiology*, 215(3), pp. 835–840 (2000).

* cited by examiner

*Primary Examiner*—Ruth S. Smith
(74) *Attorney, Agent, or Firm*—George W. Johnston; Robert A. Silverman

(57) ABSTRACT

A method of identifying, for a patient having pain of a joint, susceptibility to developing progressive osteoarthritis or loss of joint space, by determining in such patient the presence or absence of bone marrow edema about or of the joint. A determination of the presence of bone marrow edema about or of the joint identifies the patient as susceptible to developing progressive osteoarthritis or loss of joint space.

3 Claims, No Drawings

BONE MARROW EDEMA AS PREDICTIVE OF SUSCEPTIBILITY TO DEVELOPING PROGRESSIVE OSTEOARTHRITIS

FIELD OF THE INVENTION

The present invention relates to a method of identifying, for a patient having pain of a joint, susceptibility to developing progressive osteoarthritis or loss of joint space (change in cartilage of the joint) by determining in such patient the presence or absence of bone marrow edema about the joint. A determination of the presence of bone marrow edema about the joint identifies the patient as susceptible to developing progressive osteoarthritis or loss in joint space.

BACKGROUND OF THE INVENTION

Osteoarthritis is the most common form of arthritis, affecting the hands, knees, hips, spine and other joints. Characteristics of osteoarthritis include a loss of cartilage, seen as a reduction in the joint space, and osteophytes (marginal lips of bone that grow at the edges of the joints). Other forms of arthritis are also characterized by joint space loss.

Predictors of which patients will have progressive osteoarthritis, and which will have stable, non-progressive diseases is lacking, except for the use of bone scintigraphy in predicting joint space loss in the knee. However, repeated scintigraphy is not viable for following patients because of the associated repeated ionizing radiation dose. Other forms of arthritis also may have joint space loss, the prediction of which is also difficult to do or not able to be determined.

An object of the present invention is a non-invasive method, without the use of ionizing radiation, for predicting which patients are likely to have progressive osteoarthritis or joint space loss. Such a method is useful for determining which patients should receive joint protective therapies to preserve joint function.

SUMMARY OF THE INVENTION

It has been discovered that finding bone marrow edema about or of a joint of a patient is predictive of the patient developing progressive osteoarthritis in the joint. In particular, it has been found that bone marrow edema about or of a joint of a osteoarthritis patient is predictive of rapid loss of joint space width in the joint of the patient.

Accordingly, the present invention relates to a method of identifying, for a patient having pain of a joint, susceptibility to developing progressive osteoarthritis or joint space loss. The method comprises (a) performing on the patient an assay for the presence or absence of bone marrow edema about or of the joint and (b) determining in such patient the presence or absence of bone marrow edema about or of the joint. A determination of the presence of bone marrow edema about or of the joint identifies the patient as susceptible to developing progressive osteoarthritis or joint space loss.

Magnetic Resonance Imaging (MRI) is a non-invasive cross sectional imaging technique that uses magnetic fields and radio frequencies, and no ionizing radiation, to produce images of the body with excellent anatomic fidelity and soft tissue evaluations. Using specific combinations of magnetic fields and radio frequencies (pulse sequences), specific soft tissue changes can be seen, for example, the presence of water in the bone marrow about the knee.

DETAILED DESCRIPTION OF THE INVENTION

As used herein, "osteoarthritis" means a non-inflammatory or minimally inflammatory arthritis in which there is degeneration of articular cartilage, thickening, erosion and subarticular cyst formation of the underlying subchondral bone, and production of reactive marginal osteophytes about the joint, leading to deformity from joint destruction.

As used herein, "joint space loss" means a continued loss or increased abnormality of cartilage (commonly associated with joint space loss).

As used herein, "progressive osteoarthritis" means a continued loss of cartilage (commonly with joint space loss) and bone stock, as well as the increase in marginal osteophytes, subchondral bone hardening/thickening, and the onset or increase of subchondral cysts, as well as other findings known to occur with osteoarthritis. These changes may occur simultaneously or the changes may be distributed about time and areas about the joint in an uneven manner.

As used herein, "bone marrow edema" means increased water content within the bone marrow space above that in normal bone marrow.

As used herein, "area about or of the joint", for a given joint, is an area about 1 to 20 cm above and 1 to 20 cm below the articulating surface(s) of the given joint, the actual useful range dependent on the size of the joint examined.

In a preferred embodiment, the assay for the presence or absence of bone marrow edema about or of the joint is by MRI, in particular, an MRI method or pulse sequence or imaging orientation that provides imaging of the joint area where bone marrow edema can be visualized. Any MRI technology where bone marrow edema can be evaluated can be used, for example, open MRI, low field strength MRI, extremity MRI, whole body scanner MRI or the like. Other methodologies that allow for the determination of bone marrow edema would likewise provide similar information and could be used to predict progression of osteoarthritis or loss of joint space.

To determine progression of joint space narrowing, any method that measures joint space width can be used, for example, semi-flexed radiograph (x-ray method). This would also include methods that determine, directly or indirectly, the amount and/or viability of the cartilage of a joint (e.g. ultrasound, arthoscopy, etc.).

The following clinical study example illustrates, without limitation, the present invention.

EXAMPLE

Clinical Study Patient Inclusion

Patients were (1) of age greater than 50 years, or (2) had stiffness for less than 30 minutes for the target knee or (3) had crepitus of the target knee. Patients with secondary forms of osteoarthritis, or other forms of arthritis, were excluded.

In addition, patients had radiographic evidence of osteophytes and joint space narrowing of the medial compartment of the knee, which was required. Joint space narrowing (very approximately 4 mm or less joint space width for a patient of average weight (about 150 pounds)) was determined with reference to the medial joint compartment of the knee in a posterior-anterior radiograph, preferably in a semi-flexed position. The lateral joint compartment of the knee had to have at least approximately 2 mm joint space width, and could even have normal (very approximately 6 mm) joint space width. Radiographs were performed at day 0 (to establish a base line) and at 24 weeks after the baseline measurement.

36 patients were in the MRI subsection of a larger, 500 patient study, of which 34 patients were evaluable because they had complete data sets.

Study Design

A MRI was performed on the target knee of each selected patient using a 1.5 Tesla whole body scanner with a circumferential extremity coil. Imaging included T2-weighted fast spin echo images acquired in the three orthogonal planes, dual-echo fast spin echo images acquired in the sagittal plane, a multi-echo sequence with fat suppression acquired in the sagittal plane for measuring T2 relaxation time of the articular cartilage, and sagittal fat-suppressed T1-weighted three dimensional spoiled gradient echo for volumetric quantification of the cartilage. MRI was performed at day 0 and at 24 weeks.

MRI Protocol

Patients having any of the following were excluded from MRI examination:
1) Pacemaker;
2) Cardiac valve prosthesis;
3) Metallic fragments in the eyes;
4) Vascular clips less than 2 months old;
5) Aneurysm clips of any age;
6) Cochlear implants;
7) Claustrophobia;
8) Body weight in excess of 250 pounds;
9) Metallic fragments in the vicinity of the target knee other than vascular clips from venous graft harvesting older than 2 months.

Patient set up ensured correct positioning of the knee and sufficient patient comfort to limit motion artifacts and minimize the likelihood of patient dropouts on subsequent examination. The positioning of the knee in the magnet was reproducible from visit to visit to allow comparison of serially acquired images. The patients were images supine with the leg in the neutral position and the patella pointing straight up rather than in slight external rotation as is commonly the routine in clinical imaging protocols. External rotation is more difficult to reproduce on serial examinations and complicates image interpretation. Additionally, the knee was well immobilized in the circumferential extremity coil with foam padding. The same knee (target knee) was imaged at each visit.

The comfortable installation of the patient at the beginning of the study was imperative as the major source of motion artifacts is discomfort. Care was exercised in positioning the cushions and pads around the knee in the extremity coil to make the examination as comfortable as possible. Ear plugs or music through headphones was included, along with pillows, blankets, and verbal reassurance.

follows: from lateral to medial for sequences in the sagital plane, from superior to inferior for sequences in the axial plane, and from anterior to posterior for sequences in the coronal plane.

The total examination time, including the 10 minute patient set-up and prescanning, was approximately 1 hour.
1. Sagital T2-weighted fast spin echo (FSE) localizer including entire synovial cavity: 2500/60 (TR msec/TE msec), 20 cm field of view (FOV), 4 mm/0 mm (slice thickness/interslice gap), 256×128 matrix, frequency encoding (FE) anterior-posterior, 16 echo train length (ETL), 1 excitation (NEX). [Imaging time=1 min.]
2. Axial T2-weighted FSE including entire patella: 3500/60 (TR msec/TE msec), 12 cm field of view (FOV), 3 mm/0 mm (slice thickness/interslice gap), 256×256 matrix, frequency encoding (FE) anterior-posterior, 16 echo train length (ETL), 2 excitations (NEX), [Imaging time=4 min.]
3. Coronal T2-weighted FSE: 3500/60, 12 cm FOV, 3 mm/0 mm, 256×256, FE superior-inferior (SI), 8 ETL, 2 NEX, frequency-selective fat suppression, No Phase wrap (NP). [Imaging time=8 min.] Coverage included the entire femorotibial joint but not the patella.
4. Sagital dual-echo FSE: 3500/20, 60, 14 cm FOV, 3 mm/0 mm, 256×256, FE Si to avoid certain artifacts, 8 ETL, 2 NEX, wide SI saturation bands (80 Hz) to limit vascular pulsation artifacts, frequency-selective fat suppression. Coverage extended from upper pole of patella to tibial plateau.
5. Sagital multi-echo SE with fat suppression: 2500/15, 30, 45, 60, 14 cm FOV, 4 mm/0 mm, 256×160, FE, AP, wide SI saturation bands (80 Hz) to limit vascular pulsation artifacts, frequency-selective fat suppression, 1 NEX, No Phase wrap (NP). Coverage extended from upper pole of patella to tibial plateau.
6. Sagital T1-weight, three dimensional, spoiled gradient echo (3D-SPGR) with fat suppression: 58/6, 400 flip angle, 12 cm FOV, 256×192 matrix, 60 contiguous 2 mm slices covering entirety of the articular cartilage plates in the knee, 1 NEX.FE SI, with SI saturation bands to minimize pulsation artifacts, frequency-selective fat suppression. [Imaging time=12 min.].

Results

Medial Joint Space Narrowing as a Percent Change from Baseline to 24 Weeks

|  | Number Pts | Median % Change | Mean % Change (+/−SD) |
|---|---|---|---|
| Medial BME Present at Baseline | 11 | −10.89 | −6.91 (43.1) |
| No Medial BME at Baseline | 23 | 1.13 | 9.1 (27.3) |
| Medial BME Present at 24 Weeks | 12 | −7.25 | −2.2 (43.9) |
| No Medial BME at 24 Weeks | 22 | 0.69 | 7.25 (26.7) |
| Medial BME Present at Baseline or 24 Weeks | 13 | −3.6 | −1.92 (42.1) |
| No Medial BME at Baseline or 24 Weeks | 21 | 0.25 | 7.53 (15.5) |
| Medial or Lateral BME Present at Baseline | 14 | −3.8 | −4.98 (38) |
| No Medial or Lateral BME at Baseline | 20 | 2.06 | 10.15 (29.2) |
| Medial or Lateral BME Present at 24 Weeks | 16 | −3.73 | −1.5 (37.7) |
| No Medial or Lateral BME at 24 Weeks | 18 | 0.81 | 8.73 (29.4) |
| Medial or Lateral BME Present at Baseline or 24 Weeks | 17 | −3.6 | −1.33 (36.5) |
| No Medial or Lateral BME at Baseline or 24 Weeks | 17 | 0.25 | 9.16 (30.2) |

BME = Bone Marrow Edema

Image Sequences

The following sequences were preprogrammed into the MRI computer in order to speed up the examination and limit potential human error. Images were prescribed as The mean and median changes demonstrate loss of joint space (using the posterior-anterior semi-flexed knee radiographs), in the medial compartment of the knee, if 1) there is bone marrow edema at baseline and/or at 24 weeks, or if 2) the bone marrow edema is present in either the lateral or medial compartment.

Lateral Joint Space Narrowing as a Percent Change from Baseline to 24 Weeks

|  | Number Pts | Median % Change | Mean % Change (+/−SD) |
|---|---|---|---|
| Lateral BME Present at Baseline | 8 | 1.34 | 6.78 (17.1) |
| No Lateral BME at Baseline | 26 | −1.36 | −0.97 (10.9) |
| Lateral BME Present at 24 Weeks | 10 | −0.25 | 3.92 (16.4) |
| No Lateral BME at 24 Weeks | 24 | −1.01 | −0.42 (11.1) |
| Lateral BME Present at Baseline or 24 Weeks | 11 | −0.31 | 3.49 (15.6) |
| No Lateral BME at Baseline or 24 Weeks | 23 | −1.26 | −0.47 (11.4) |
| Medial or Lateral BME Present at Baseline | 14 | 1.34 | 7.37 (16.7) |
| No Medial or Lateral BME at Baseline | 20 | −2.05 | −3.7 (6.33) |
| Medial or Lateral BME Present at 24 Weeks | 16 | 1.16 | 6.13 (16.1) |
| No Medial or Lateral BME at 24 Weeks | 18 | −2.05 | −3.83 (6.31) |
| Medial or Lateral BME Present at Baseline or 24 Weeks | 17 | −0.18 | 5.3 (15.9) |
| No Medial or Lateral BME at Baseline or 24 Weeks | 17 | −1.96 | −3.59 (6.41) |

BME = Bone Marrow Edema

The mean and median changes demonstrate loss of joint space (using the posterior-anterior semi-flexed knee radiographs), in the lateral compartment of the knee, if 1) there is bone marrow edema at baseline and/or at least 24 weeks, or if 2) the bone marrow edema is present in either the lateral or medial compartment.

The findings show that bone marrow edema is predictive of changes in the joint, such as cartilage, and in particular, of joint space narrowing. Minor differences from the lateral compartment data, compared to the medial joint space data, relate to the medial compartment requiring osteoarthritis, whereas the lateral compartment could have a normal joint space (little to no evidence of osteoarthritis in the lateral compartment) to one that was at least 2 mm (consistent with osteoarthritis in this patient set), by knee posterior-anterior radiograph.

What is claimed is:

1. A method of identifying, for a patient having pain of a joint, susceptibility to developing progressive osteoarthritis or the loss of joint space comprising (i) performing on the patient an assay for the presence or absence of bone marrow edema about or of the joint, and (ii) determining in such patient the presence or absence of bone marrow edema about or of the joint, wherein a determination of the presence of bone marrow edema about or of the joint identifies the patient as susceptible to developing progressive osteoarthritis or the loss of joint space.

2. The method of claim 1, wherein the joint is a knee.

3. The method of claim 2, wherein the assay is performed by magnetic resonance imaging.

* * * * *